United States Patent
Ehrenreich

(10) Patent No.: US 8,170,657 B1
(45) Date of Patent: May 1, 2012

(54) DELIVERY CATHETERS FOR LIGHT ACTIVATED AGENTS

(75) Inventor: Kevin J. Ehrenreich, San Francisco, CA (US)

(73) Assignee: Abbott Cadiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/191,124

(22) Filed: Aug. 13, 2008

(51) Int. Cl.
*A61N 1/30* (2006.01)

(52) U.S. Cl. ............. 604/20; 604/21; 604/22; 600/178; 600/179; 600/180; 433/29

(58) Field of Classification Search .............. 604/4.13, 604/20–22; 600/178–182; 433/29
See application file for complete search history.

(56) References Cited

U.S. PATENT DOCUMENTS

| | | | |
|---|---|---|---|
| 4,009,382 A | | 2/1977 | Nath |
| 4,761,054 A | * | 8/1988 | Ishimori et al. ............... 385/117 |
| 4,900,303 A | * | 2/1990 | Lemelson ..................... 604/514 |
| 5,412,750 A | | 5/1995 | Nath |
| 5,454,782 A | * | 10/1995 | Perkins ........................... 604/20 |
| 5,608,834 A | | 3/1997 | Van Leeuwen |
| 5,702,344 A | * | 12/1997 | Silverstein .................... 600/104 |
| 5,709,653 A | | 1/1998 | Leone |
| 5,800,478 A | | 9/1998 | Chen et al. |
| 5,830,209 A | * | 11/1998 | Savage et al. .................. 606/15 |
| 6,254,573 B1 | * | 7/2001 | Haim et al. ................... 604/157 |
| 6,296,608 B1 | * | 10/2001 | Daniels et al. ................ 600/104 |
| 6,484,052 B1 | * | 11/2002 | Visuri et al. .................... 604/20 |
| 6,749,623 B1 | | 6/2004 | Hsi et al. |
| 6,807,295 B1 | * | 10/2004 | Ono .............. 382/154 |
| 6,811,562 B1 | | 11/2004 | Pless |
| 7,131,963 B1 | | 11/2006 | Hyde |
| 7,252,677 B2 | | 8/2007 | Burwell et al. |
| 7,344,528 B1 | | 3/2008 | Tu et al. |
| 2002/0183738 A1 | * | 12/2002 | Chee et al. ....................... 606/41 |
| 2004/0230156 A1 | | 11/2004 | Schreck et al. |
| 2005/0031281 A1 | | 2/2005 | Nath |
| 2005/0070844 A1 | * | 3/2005 | Chow et al. ................ 604/95.04 |
| 2005/0107706 A1 | * | 5/2005 | Zuluaga et al. ............... 600/473 |
| 2006/0211918 A1 | * | 9/2006 | Lieponis ....................... 600/182 |
| 2007/0090272 A1 | | 4/2007 | Wang |
| 2008/0025943 A1 | | 1/2008 | Michal et al. |
| 2008/0033339 A1 | | 2/2008 | Tulip et al. |

OTHER PUBLICATIONS

StockerYale Inc., Laser Line Generators, LEDs, Specialty fibers, downloaded www.stockeryale.com, May 29, 2008, 1 page.
StockerYale Inc., "Custom-Engineered LED Solutions", downloaded www.stockeryale.com, May 29, 2008, 2 pages.

\* cited by examiner

*Primary Examiner* — Bhisma Mehta
*Assistant Examiner* — Edelmira Bosques
(74) *Attorney, Agent, or Firm* — Squire Sanders (US) LLP

(57) ABSTRACT

A delivery catheter for delivery, then photo-activation of photo sensitive material has a photo-sensitive substance-delivery part and an activation part. The catheter delivers substances such as biomaterials to a target site, followed by illumination of the target using optics located at the distal tip of the catheter which are optically coupled to an extracorporeal light source. In another aspect a deployable light-delivery catheter is disclosed that can illuminate a large area of tissue.

12 Claims, 6 Drawing Sheets

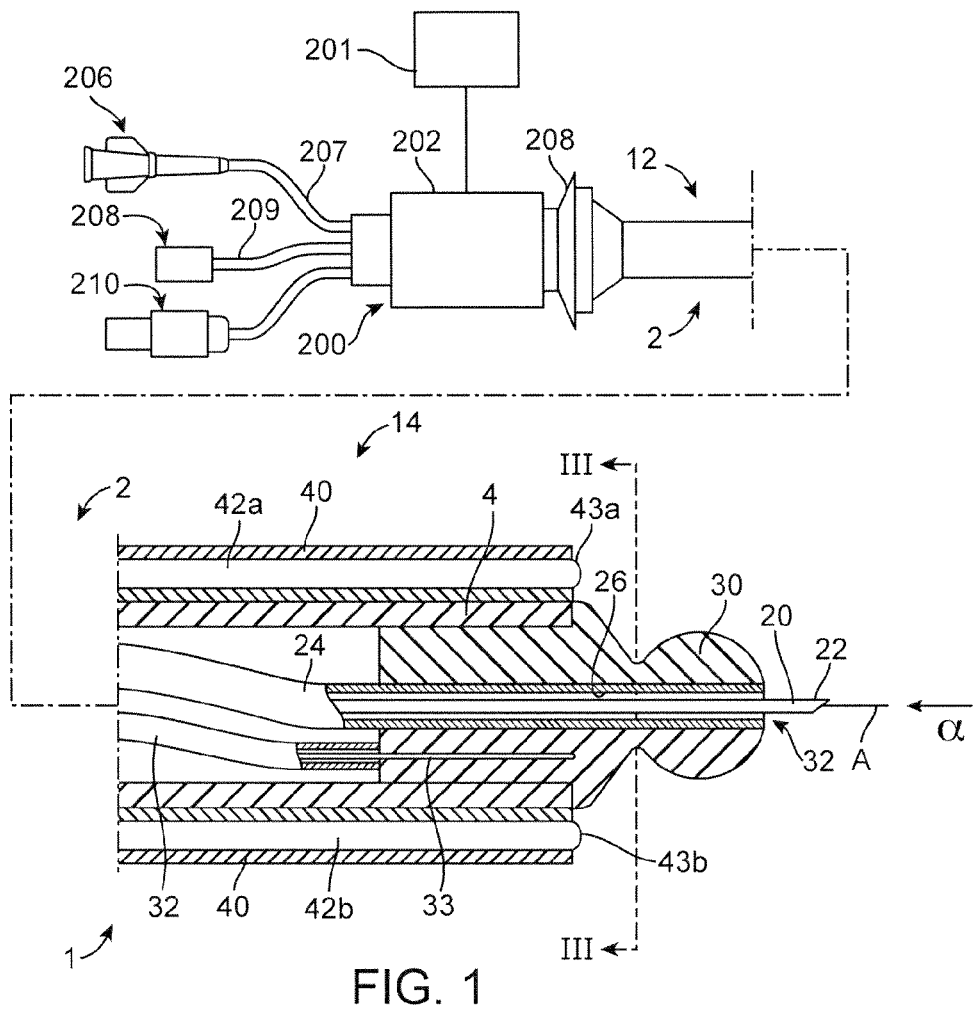
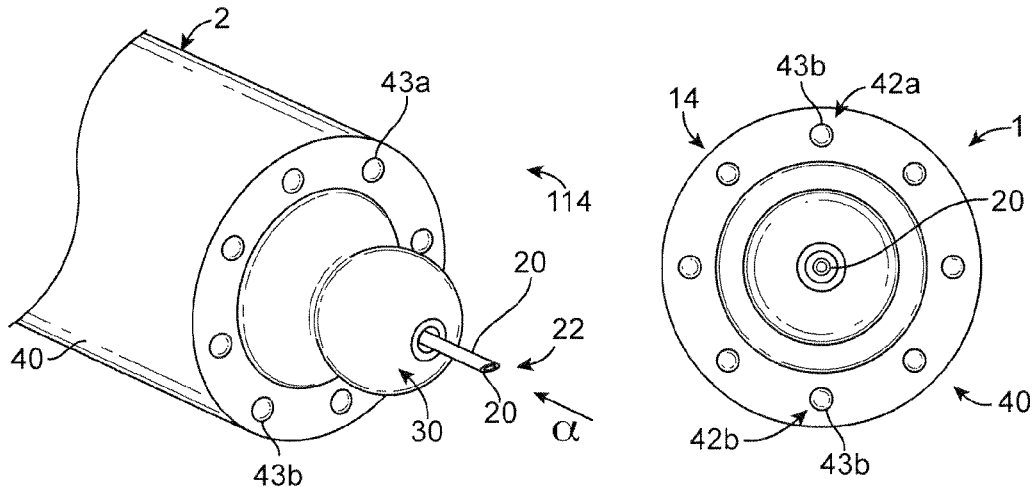
FIG. 1
FIG. 2
FIG. 3

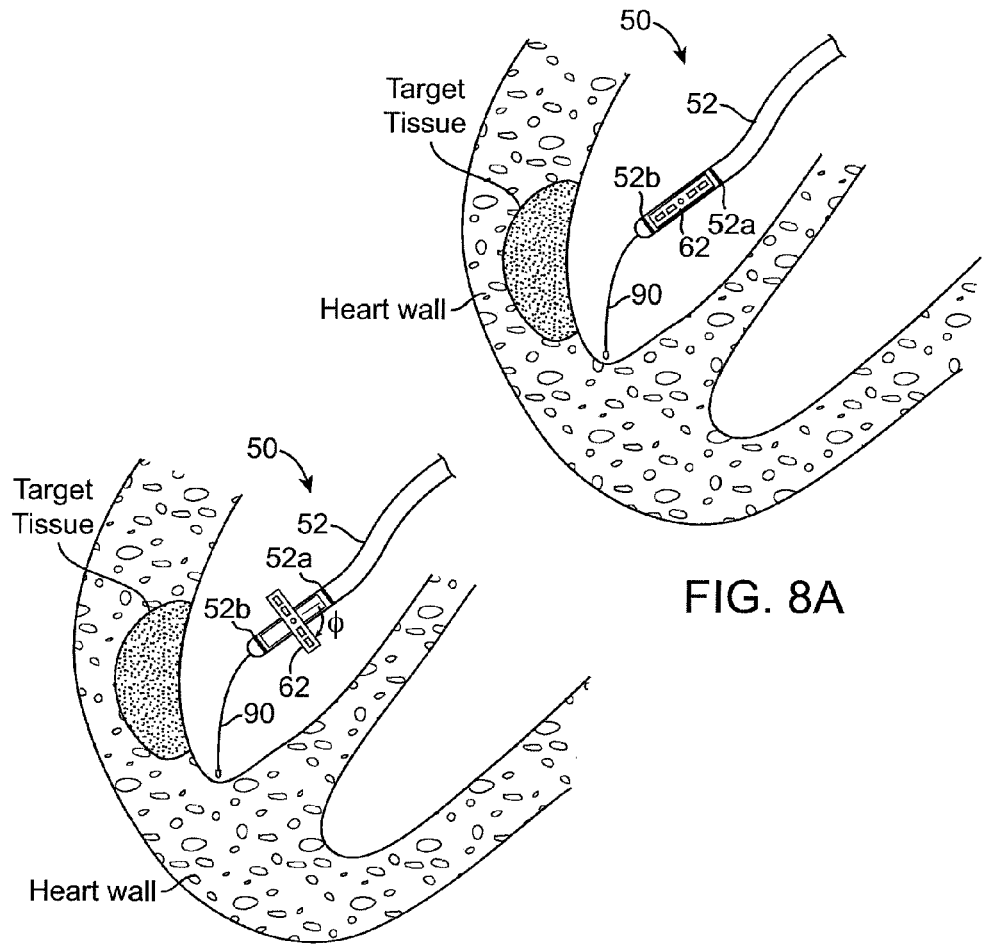
FIG. 8A
FIG. 8B
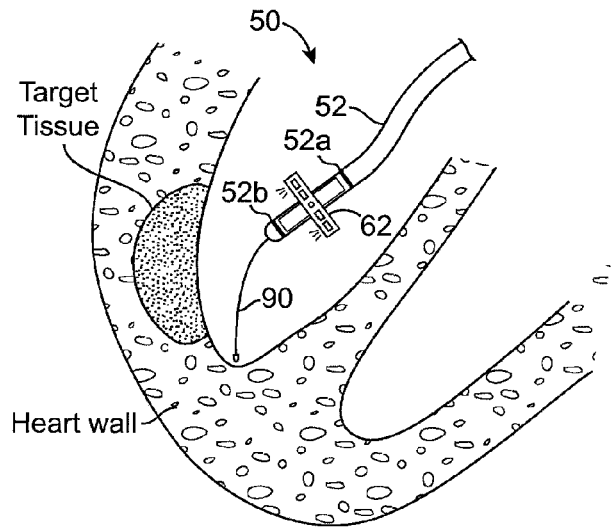
FIG. 8C

DELIVERY CATHETERS FOR LIGHT ACTIVATED AGENTS

BACKGROUND OF THE INVENTION

1. Field of the Invention

This invention relates to methods and devices for treating tissue using photo-sensitive substances, such as biomaterials, using a catheter.

2. Description of the Related Art

Ischemic heart disease typically results from an imbalance between the myocardial blood flow and the metabolic demand of the myocardium. Progressive atherosclerosis with increasing occlusion of coronary arteries leads to a reduction in coronary blood flow, which creates ischemic heart tissue. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that can result from the sudden lack of supply of oxygen and other nutrients. The lack of blood supply may be caused by a closure of the coronary artery (or any other artery feeding the heart) which nourishes a particular part of the heart muscle. The cause of this event is generally attributed to arteriosclerosis in coronary vessels.

Infarct myocardial tissue may be treated by implanting cells, such as mesenchymal stem cells, skeletal myoblasts, bone marrow mononuclear cells, etc., which will facilitate the revitalization of the infracted heart tissue. Hereafter, these types of materials, as well as solutions containing them, will be referred to as therapeutic agents, agents, biomaterials, or photo-activated substances. Delivery of therapeutic agents into the infarct tissue in a minimally-invasive way generally requires that a catheter access the Internal heart chamber wall in which the infarcted area exists.

Bioscaffoldings formed of two components and applied in situ to the left heart ventricle can be used to treat post-myocardial infarction tissue damage. "Bioscaffolding", "two-component gelation system" and "gelation system" are terms that are used interchangeably in this context, and are described more fully in U.S. Pub. No. 2008/0025943. Examples of two-component gelation systems include, but are not limited to, alginate construct systems, fibrin glues and fibrin glue-like systems, self-assembled peptides, synthetic polymer systems and combinations thereof. Each component of this two-component gelation system may be co-injected to an infarct region by a dual-lumen delivery device. Examples of dual-lumen delivery devices include, but are not limited to, dual-needle left-ventricle injection devices, dual-needle transvascular wall injection devices and the like.

Another Type of Therapy exists to introduce chemical compound drugs, sometimes called photosensitizers, into tissue and then excites the hotosensitizer in order to enable an energy transfer from the photosensitizer to a nearby oxygen molecule. This produces an excited singlet state oxygen molecule that reacts with nearby biomolecules. This reaction can cause localized damage in target atherosclerotic tissue, for example. The therapy can also be applied in oncology, and may be used to kill cancer cells after they have absorbed a pre-delivered photosensitizer. This therapy thereby provides beneficial effect to the patient.

SUMMARY OF THE INVENTION

According to one aspect of the invention, devices are provided which may be used to deliver biomaterials for cellular cardiomyoplasty. The biomaterials intended for delivery using these devices include photo-polymerizable gels and cells such as autologous or allogeneic adult stem cells, or embryonic stem cells. This includes various embodiments of hydrogel biomaterials for increased efficacy of cellular cardiomyoplasty, improved cell retention at the delivery site, increased cell survival, improved myocardium mechanical properties, and to serve as depots for cytokines. Other materials may be delivered in combination with the photo-polymerizable gels in accordance with these embodiments, as will be appreciated. The disclosure provides devices that are capable of injecting the biomaterials to a target location within the myocardium, and subsequently delivering energy from an optical source to activate the biomaterials. The device also includes features to minimize thermal damage caused by light energy.

The invention provides devices and methods for photo-activated biomaterials, as well as agents that are intended to induce cell necrosis, e.g., as when treating a tumor. According to one aspect of disclosure the material is not photo-activated until after it has been deposited within a tissue. As such, the risks of inducing thrombosis are reduced.

Words containing the term "photo", such as photosensitive or photo-activated are intended to refer to any band of light that is known, either in the art or as disclosed herein, to have beneficial effects for treatment of conditions using substances that polymerize when exposed to light energy. Accordingly, it will be appreciated that the term "photo" should not be understood as implying that only a particular band of light applies, e.g., visible light, unless the specific context indicates otherwise. As will be apparent from the disclosure, the invention applies to light bands such as IR, visible and UV light. In a preferred embodiment, IR light is used since its longer wavelength allows it to penetrate deeper into tissue. In this way light capable of activating photo-sensitive substances may be transmitted deeper into tissue while reducing risks of thermal damage to tissue closer to the surface.

According to another aspect of the invention, there is a method and device for injecting and then photo-activating photo polymerizable gels. According to some of these embodiments, a catheter may deliver the gel and light, but separates the two so that the gel is not activated until it is implanted or deposited in the target tissue.

According to another aspect of the invention an improvement over a dual-lumen catheter for treating infarcted heart tissue is provided. In some embodiments a delivery catheter includes a lumen configured to deliver a single photosensitizer, e.g., a photocrosslinkable one component hydrogel (as opposed to a two-component gel). The photo-activated biomaterial is isolated from the light energy until it has been implanted into the tissue. As compared to a dual-lumen catheter which has previously been used to perform a similar treatment, but required a rapid and reproducible mixing of the two or more substances at the tip of the catheter, the method according to the invention may perform the steps where only one lumen is required, a single substance is injected and then a light source is used to activate the substance. In a preferred embodiment the light source and delivery needle may be integrated so that injection and activation of the photosensitive material may be performed at essentially the same time.

This invention includes one or more of the following benefits. A premature activation of the photosensitize material is mitigated compared to when multi-component gels are used. A simplicity of a design permits single injection and immediate activation "with the flip of a switch". Risks of thrombotic events may be significantly reduced compared to multi-lumen and multi-component gel techniques.

According to another aspect of the invention, a treatment using photosensitive substances may include depositing then activating the photo-sensitive material using a single catheter. Alternatively the treatment proceeds by first placing photosensitive material within a body, e.g., intravenously or directly, e.g., using a needle catheter, and then delivering a light emitting catheter to a treatment area.

According to another aspect of the invention, a light emitting catheter includes a mechanism for deploying a light emitting member. Such a member may be desirable as it can dramatically increase the coverage area for light when a large area of tissue is being treated, e.g., such as the right or left ventricle of the heart.

The methods and devices disclosed herein may be used in connection with procedures intended to induce cell growth, e.g., treating infarct tissue, or cell death, e.g., treating a tumor. Accordingly, it will be appreciated that the invention includes methods and devices used in connection with either of these types of procedures.

According to another embodiment, a catheter that injects and light activates may prevent washout (meaning an event where injected material exits from the puncture hole when the needle is removed, as opposed to staying with the tissue as intended). When a material was injected, the needle was removed and then light used to activate material, e.g., using a separate device. The material may exit when the needle is removed. If a photo-polymerizable gel is used in connection with one or more embodiments of the invention, activation using light energy while the needle is embedded will prevent material from exiting through the puncture caused by the needle because gelation occurs while the needle is embedded within the tissue. Thus a method of treating tissue and catheter having a light emitting end and needle addresses the need for reducing instances of washout as in, for example, when treating heart tissue which is moving continuously as the heart beats. Such a method and apparatus also reduces chances of other complications since the amount of time spent within the heart may be reduced by a catheter that both injects and photo-activates an injected substance.

Embodiments of the invention include one or more of the following additional benefits and advantages.

According to another embodiment, a catheter includes a body having a piercing tip disposed at a distal end and a proximal end configured for being selectively placed in fluid communication with a substance. The body forms a lumen for deliver of the substance from the proximal end to an exit located adjacent the tip. The catheter also includes a light guide having a light-emitting end disposed at the distal end and a proximal end coupled to a light source. The light source may be a lamp light or laser light. The catheter may have a light guide and light source as part of the catheter, i.e., integrated with the catheter, or the catheter may correspond to one in which the guide and associated optics may be attached or removed from the catheter depending on need.

According to another embodiment, a catheter has a needle disposed at a distal end and configured for delivery of a photosensitive substance directly into tissue and a light guide having an illumination end disposed at the distal end. The illumination end is configurable between a deployed and/or stowed position according to these embodiments.

According to another embodiment, a catheter includes means for embedding a photosensitive agent into tissue, and means for activating the photosensitive agent.

According to another embodiment, a catheter having a distal and proximal end includes a light emitter at the distal end and a deployable needle at the distal end. A photo-sensitive material can be injected, and the material exposed to activating light while the needle remains embedded within the tissue. As such, possible washout of the photo-sensitive material may be prevented.

According to another embodiment, a method of therapy includes the steps of placing a distal tip of a catheter proximal a tissue, thereby placing both an energy source and needle proximal the diseased tissue, injecting a photosensitive substance into the tissue using the needle, and photo-polymerizing the injected substance using the energy source.

According to another embodiment, a method of therapy using a catheter having a distal end comprises the steps of extending a needle tip from the distal end, embedding the tip into a tissue, dispensing a photosensitive drug, biomaterial, agent, etc. via the embedded tip, and emitting light from the distal end to thereby activate the drug.

According to another embodiment, a method of treating tissue includes the steps of disposing an injection catheter proximal a tissue, injecting photosensitive biomaterial into the tissue, and emitting light from the injection catheter to activate the biomaterial.

According to another embodiment, a catheter suited for activating photo-activated agents includes a catheter shaft extending from a distal to a proximal end, the shaft having a shaft axis, and a plurality of light-emitting members disposed at the distal end and movable relative to the shaft axis.

According to another embodiment, a catheter includes a light module and means for directing light towards tissue at its distal end. The means for directing light may include disposing the light module on a rotating member, mounting an LED chip on a rotating member and/or a means for rotating and energizing the light module.

According to another embodiment, a method for photo-activating agents includes the steps of placing a catheter near a target tissue, deploying a light member from the catheter, and emitting light from a plurality of light sources disposed on the light member.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 1 is side view, partial cross-section of a needle catheter.

FIG. 2 is a partial perspective view of a distal end of the needle catheter of FIG. 1.

FIG. 3 is a front view of the needle catheter taken at section in FIG. 1.

FIGS. 8A, 8B and 8C depict a method of delivery of light energy to target tissue. According to these embodiments, a catheter may be delivered to a treatment site after the tissue has accumulated or absorbed photo-sensitive material in order to photo-activate agents in the tissue.

DETAILED DESCRIPTION OF THE INVENTION

Figure 4A:
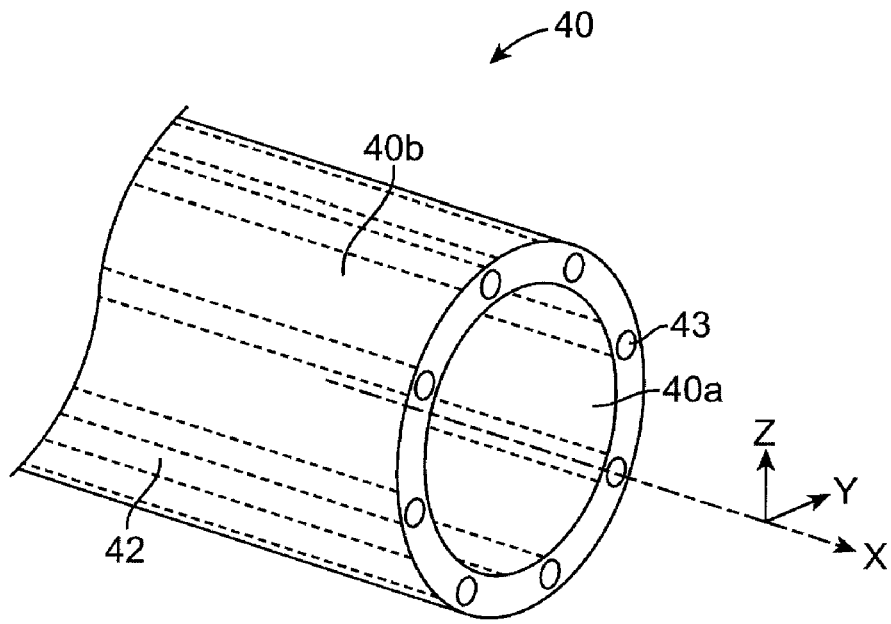
FIGS. 4A-4B are perspective views of two embodiments of an optical bundle contained within a light member. The light member may be separable from a catheter, i.e., connected as a functional unit and removed when not needed for a procedure or passed over the catheter when needed, integrated within a catheter unitary or composite shaft design, or retrofitted to an existing catheter.

According to the disclosure, a catheter may include both a needle and a light guide for directing light to a target tissue using an extracorporeal light source. This aspect of the disclosure describes embodiments in which the light is emitted from a light member that is separately configurable with a needle catheter, or integrated into a needle catheter. In an illustrated embodiment a tubular-like structure having embedded fiber-optics is described. The tubular member may be adjusted relative to the catheter. In a second aspect of the disclosure, a light delivery catheter is described. This catheter, which may be steered over a guide wire, utilizes a plurality of on-board light sources, e.g., LED. The catheter is capable of emitting light over a greater area of tissue and offering greater control and accuracy for directing light to tissue.

FIG. 1 illustrates a partial side view of a needle catheter 1, which has a distal section 14 shown in partial cross-section and a proximal section 12. A shaft or body 2 extends from a controller 200 to a tip 30 of the catheter 1. A jacket 4 extends over the distal portion 14 of the catheter 1 and is flexible in bending yet stiff in compression. This jacket 4 is secured to a tip 30. The jacket 4 may also be constructed as a composite piece that includes an inner cage. The catheter may have one or more tendons 33 (movable within tubular members 32) which are used to steer or deflect the catheter 1 as it is passed through an anatomy or positioned within an anatomical cavity. The catheter 1 may be steered using a steering portion 208 and handle 202 provided at the proximal end 14 of a controller 200. The controller 200 also includes functional units 206, 208 and 210. In a preferred embodiment these functional units correspond to an optical coupler 208 for transmitting light to a fiber optic bundle (as discussed in greater detail, below), a diagnostic device 210 and a port 206 that receives an injection needle 20. A spherical shape may be used for the tip 30 in order to improve the acoustic properties of the tip 30 when the catheter 1 is imaged by ultrasound, i.e., so that the tip 30 can be easily tracked as it is passed through anatomy. The spherical shape may also improve maneuverability through tortuous anatomy. Further examples are provided in U.S. Pub. No. 2007/0167822. While shape 30 is preferred other tip designs may also be used.

A tubular member 24 extends from the proximal end 12 to the distal end 14. A bore 26, formed by tubular member 24, is sized to provide passage for the injection needle 20, which in FIG. 1 is shown protruding out from an opening 32. Lumen 26 extends from opening 32 at the tip 30 to proximal section 12 where it is in communication with tubular member 207, which connects to port 206. Injection needle 20 may be carried with catheter 1 as it is delivered to a target site, or inserted and then passed over the length of the catheter 1 after the catheter 1 has reached a target tissue.

Figure 5:
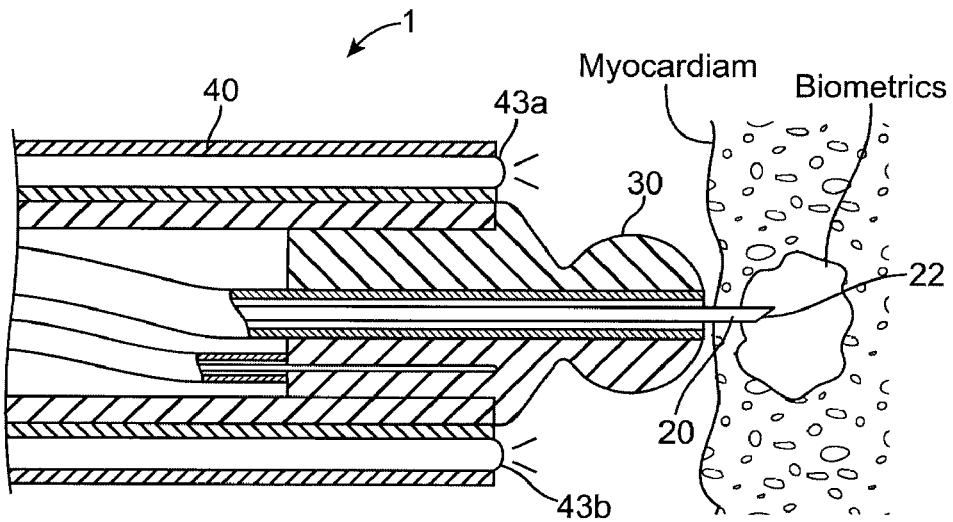
FIG. 5 depicts a method for treating tissue using a delivery catheter according to one embodiment. In this example, an agent, e.g., a photo-polymerizable gel, is inserted into a myocardium wall and then light energy is applied to the tissue to activate the gels. The light source may be an extracorporeal light source according to these methods.

The needle 20 is hollow and may include a beveled tip 22 so that it can easily pierce tissue. An opening 20a located at or near the tip 22 provides access to the lumen formed by the hollow needle 20 body. As depicted in FIGS. 5-6, photosensitive biomaterial is dispensed from the opening 20a after the needle 20 has become embedded in tissue, in this case a wall of the myocardium. The needle 20 is opaque so that photosensitive material in the needle 20 does not become exposed to light. Port 206 may be replaced by a port that allows an inserted needle to rotate, and a secondary needle passed in and out of an opening in the injection needle for purposes of providing a wider region of coverage for photosensitive injected biomaterials into a target tissue (without having to remove then reinsert the needle at a new location in order to ensure adequate coverage for all diseased tissue). Examples of this type of injection needle type may be found in U.S. application Ser. No. 12/022,047 filed Jan. 29, 2008. One type of needle port or adapter may be replaced by another using the same catheter and, in some cases, during the same procedure. The needle 20 may be extended and retracted through an opening 32 located at the tip 30 by a push and pull motion applied at the proximal end, i.e. at a needle portion located at port 206. In other embodiments, the needle 20 may be selectively displaced by a worm gear or other suitable control mechanism (connected as a functional unit to the controller) if more precise extension-retraction control is desirable to ensure the needle 20 is placed at the correct depth within a tissue (see FIG. 5). The distal section 14 may also include anchoring mechanisms that may be useful to prevent the tip 30 from becoming dislodged from the wall of the myocardium during a procedure. Examples of these devices are described in U.S. application Ser. No. 12/022,047 filed Jan. 29, 2008.

Needle catheter 1 includes a unit that is capable of transmitting light from the proximal section 12, i.e., a light source coupled to optical coupler 208, to the distal section 14. According to these embodiments the catheter 1 may therefore be used to both implant or inject photosensitive material, as well as administer light therapy to activate the material. As compared to a method in which, e.g. material is injected locally (or administered intravenously) and then a separate light source is administered according to a different procedure, a method of therapy is offered in which both tasks are accomplished at essentially the same time. A single invasive procedure may accomplish what has required multiple invasive procedures in the past. Thus, for example, in the case where a beating heart is being treated, a method according to the disclosure includes the steps of injecting material directly into the target tissue and then activating said material by the same device that injected the substance. The method offers advantages including a single, simplified procedure as opposed to multiple procedures, reduced risks of adverse effects such as thrombosis and greater control over the area that is intended for treatment.

Referring to FIGS. 1-4, a light member 40 is disposed over jacket 4. Member 40 is tubular and includes a plurality of light guides 42 which extend over the length of member 40 and terminate at an optical coupling for a light source connected at the proximal section 12 of the catheter 1. Member 40 may be integral with jacket 4 or separately affixed to the outer surface of jacket 4. In the latter case, member 40 may be part of a functional unit that may be connected to an existing catheter when needed, and removed when not needed. The member 40 may be used to transmit laser light or lamp light, i.e., multiple bands or a narrow band of light. As noted earlier, fiber optic light guides 42 may be used to transmit light. Owing to their flexibility in bending and small size fiber optics are preferred. The light sources, and bands of light include, but are not limited to a xenon lamp, or a pulsed laser light, and light bands IR, near IR, visible light or UV light. The light source may be capable of multi-spectrum light emission. Optical couplers suited for transmitting lamp light or laser light over a narrow or wide bandwidth are known in the art and may be readily modified for use with a needle catheter in view of this disclosure.

Referring to FIGS. 1, 2, 3 and 4 the light guides are provided by fiber optics 42. The terminal ends of these fibers, e.g., end 43a and 43b, are arranged to emit light forward of the catheter 1, although it will be appreciated that the fibers may emit light such that the primary delivery intensity is in a transverse or partially transverse direction. Preferably, optical fibers 42 are arranged circumferentially about the needle 20, as best depicted in FIG. 3. This allows catheter 1 to provide light everywhere surrounding an injection site for the needle and reduces if not eliminates shadows from forming on the target tissue. As shown in FIG. 3 there are eight optical fibers arranged evenly about the needle 20. There can be more or less optical fibers used. Factors that can influence the selection of, and/or placement of the optical fibers include the coverage area over the tissue, e.g., wide/narrow focus, dispersed light, desired energy flux, the available space at the distal end 14 and the degree to which the optical fibers 42 may effect the stiffness characteristics of the catheter 1.

Figure 4B:
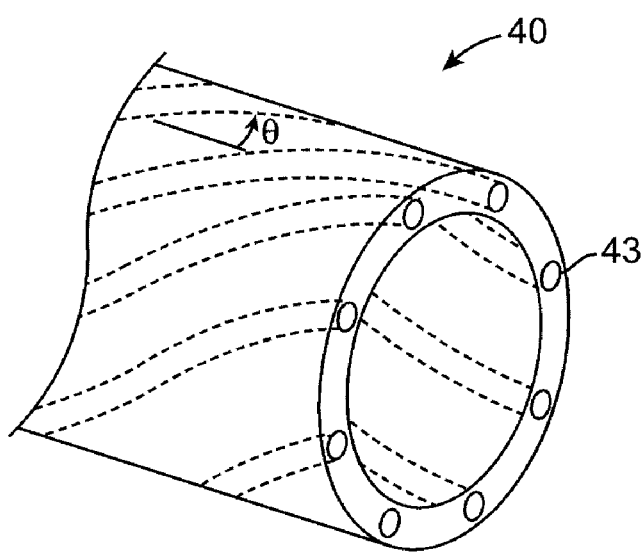

Referring now to FIGS. 4A-4B, there are depicted two embodiments of light member 40. An outer sleeve or sheath 40b and inner sleeve or sheath 40a are suitably chosen to reduce light transmission losses over the length of the catheter shaft 2. According to the two illustrated embodiments, member 40 includes eight separate optical fibers 42, which terminate at a light-emitting end 43 at the distal tip of member 40. The ends 43 are arranged so that light is primarily directed in the X-axis direction although it is contemplated that a significant portion of light may be directed in the Y- or Z-axis direction within the scope of the invention.

The arrangement of the optical fibers 42 over the length of the catheter 1 may be varied to achieve a particular degree of flexibility, or maintain such flexibility in the catheter that receives the member 40 over its outer shaft. In the illustrated embodiment, FIG. 1, catheter 1 may have a same or different flexural rigidity about the Y-axis and Z-axis (FIG. 4A). Thus, catheter 1 may require a high degree of flexibility in bending about any axis transverse to the X-axis so that the catheter can easily navigate through tortuous anatomy. Several evenly spaced optical fibers 42 extending longitudinally over the length of the member 40, as depicted in FIG. 4A, may increase the bending stiffness of the catheter 1 that receives member 40. This can be undesirable as it can make it difficult to navigate the catheter 1 with member 40 through tortuous anatomy. For the embodiment depicted in FIG. 4A, the internal forces induced by a bending moment will be carried by the relatively stiff (in axial tension and compression, that is) optical fibers 42. Thus, it may be desirable to arrange the strands 42 in such a manner as to minimize any increase in the bending stiffness when the member 40 is integrated with the catheter 1. For example, the optical fibers 42 may be arranged in a helical or spiral pattern having a helix angle θ, as depicted in FIG. 4B. When a spiral arrangement is used, less fiber optic material (as a percentage %) carries the bending loads. Hence, with a spiral configuration several optical fibers may be used without causing an unacceptable increase in the catheter's bending stiffness. The fiber optics may be arranged in varying spiral patterns (i.e., θ is not constant among each strand) or other non-longitudinal arrangements (FIG. 4A depicts a longitudinal arrangement of fibers) to minimize effects to the bending stiffness of the catheter 1 over one or more longitudinal sections of the catheter.

In the illustrated embodiments the fiber optics ends 43 are arranged so that substantially all of the transmitted light exits these light guides as direct light primarily along the X-axis. This is preferred, although not necessary, for a catheter 1 where biomaterials are injected using a needle and then this material is activated by a light source while the needle remains embedded within the tissue (see FIG. 5). In some embodiments, the dispersion of photosensitive biomaterials in the tissue may be more extensive, in which case a wider distribution of light is desirable. Or the target tissue may be confined to a small area, in which case more focused light may be desired, e.g., to reduce power requirements for the light source.

In some embodiments the light member 40 may be configured to be moved forward so that its light-emitting ends 43 are adjacent tissue, or moved rearward so that more tissue is exposed to direct light. According to some embodiments, the catheter may be configured such that a displacement of the ends 43 relative to the opening 32 (see FIG. 1) may be pre-matched to the corresponding radius of tissue receiving direct light emitted from ends 43 (assuming the opening 32 abuts the tissue surface, see FIG. 5). Alternatively, or in addition, a correlation may be made between the distance of displacement of the member 40 relative to the tip 30 and the energy flux on the tissue receiving direct light (again, assuming the opening 32 abuts the tissue surface, see FIG. 5). Thus, a guide 201 can be incorporated at the controller 200 that correlates the operator's displacement of the member 40 over the catheter shaft 2 to the tissue surface area receiving direct light.

Other optical elements/techniques may be used to achieve similar purposes. For example, the ends of the elements may be formed as convex or concave lens types, an index of refraction may be chosen to affect the manner in which light is collected/distributed, the ends 43 may be optically connected to a forward diffusion lens, etc. Refracted or reflected light, or a combination thereof may be used to achieve a particular light distribution over the target tissue. According to these embodiments, the optics associated with member 40 are intended to increase or reduce the area of tissue receiving direct light, which may be desirable from the perspective of photo-activating a larger amount of tissue or increasing the energy flux without increasing power requirements or to make up for transmission losses.

FIG. 5 depicts a cross-sectional view of the distal end of catheter 1 with the needle 20 penetrated into the myocardium wall and after biomaterials have been injected into the tissue via the needle opening 20a. In a method for depositing and then activating biomaterial, e.g., photo-polymerizable gels and cells such as autologous or allogeneic adult stem cells, or embryonic stem cells, the first step is to deliver the catheter tip 30 to the target tissue, in this case the myocardium wall. According to this embodiment the catheter 1 and member 40 are integral and thus delivered together. The catheter tip 30 is tracked through the anatomy using ultrasound or another suitable imaging technique. Once properly positioned adjacent to the myocardium wall, the needle 20 may be inserted into port 206 and then passed up to the opening 32, or the needle 20 may be transported at the same time as the catheter 1, as discussed earlier. Next, the needle 20 is penetrated into the tissue at the desired depth. Since there may be a high degree of motion of the myocardium during this time, the catheter may include a deployable anchor that can assist with holding the tip 30 at the desired location during the procedure. The catheter may also incorporate sensors or other means for determining when the tip 30 is placed at the desired location.

After the needle 20 has been properly located within the tissue, the biomaterial is delivered through the needle lumen and deposited within the tissue. The light source, e.g., pulsed laser or xenon lamp, is then energized and light transmitted over fiber optics 42. This light activates the biomaterial. In one example, IR light is used to penetrate deep into the tissue to activate biomaterial. In some embodiments the light energy may be activated and tissue illuminated at the same time that the biomaterial is being injected into the tissue. This may be desirable over a two-step process as it can reduce the amount of time needed at the treatment site. In alternative embodiments, light with a wavelength in the visible and ultraviolet electromagnetic spectrum may be used for biomaterial activation. It will also be appreciated that a number of light sources exist beyond those previously mentioned for delivering different light sources exist beyond those previously mentioned for delivering different light wavelengths. For example, numerous electroluminescent, gas discharge, and high-intensity discharge lamps exist that are capable of producing the desired wavelength of light. The light wavelengths and light sources can be identified and chosen based on the specific biomaterial and application that is used.

Figure 6A:
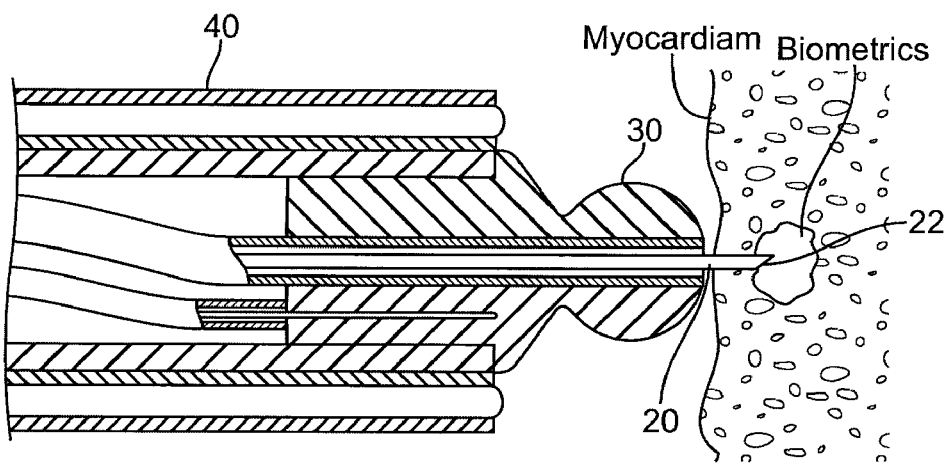
FIGS. 6A-6B depicts a method for treating tissue using a delivery catheter according to another embodiment. As illustrated, a light guide is moved closer to a treatment site after a substance has been injected into tissue, and then the substance is photo-activated while the needle remains embedded within the myocardial wall. The light source may be an extracorporeal light source according to these methods.
Figure 6B:
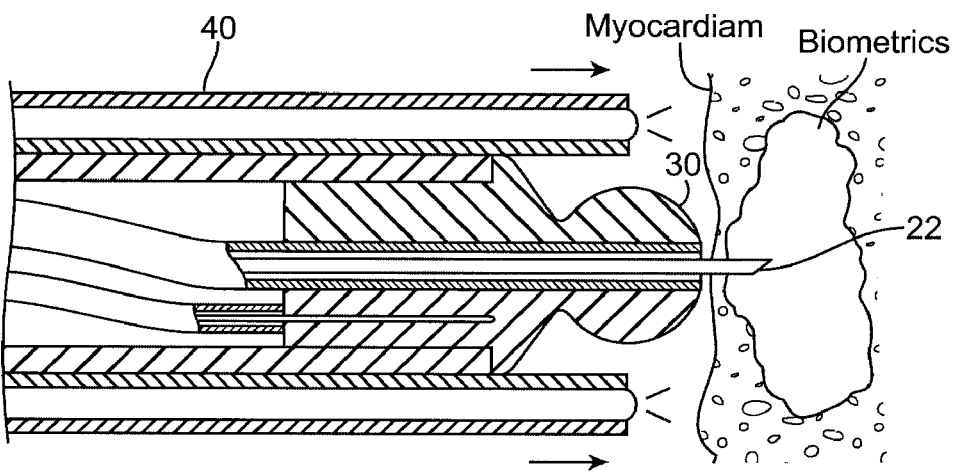

Referring to FIGS. 6A-6B, in an alternative embodiment member 40 may be slidable over the catheter shaft 2 such that it may be positioned closer or further from the myocardium wall. Thus, in some embodiments a catheter is provided in which the coverage area for light may be focused over a narrow area, or over a broad area, depending on need (as discussed above). For example, if a photo-sensitive material is dispersed over a wide area, the member 40 may be retracted or moved away from the tissue surface so that direct light is received over more tissue surface but where the accompanying lower intensity of light energy is adequate to activate the substance in the tissue. In another example, a biomaterial may be injected deep within the tissue where it is localized to a particular area. In this case, a higher intensity light directed over a smaller area may be preferred. In this case, the member 40 is brought closer to the tissue wall as depicted in FIG. 6B.

According to the embodiments depicted in FIGS. 6A-6B, the catheter is positioned at the tissue, the needle 20 penetrates the tissue, and biomaterial is injected (as before). Then, the member 40 is slide forward so that the ends 43 of the optical strands are located adjacent the tissue. In some embodiments, methods of therapy including sliding the member 40 over the shaft 2 may be accomplished in two steps, e.g., inject material then photo-activate material, or these steps may occur at the same time. In either case the steps may include positioning the catheter 1 at the tissue, inserting the needle 20 into the tissue, and then sliding the member 40 forward (or rearward) so that the ends 43 are properly positioned relative to the tissue to provide the desired depth, energy flux per unit area, or surface-area coverage of direct light energy for photo-activation. The steps may further include an operator pushing and/or pulling, respectively, a proximal end component coupled to the member 40 so as to achieve a desired distance between the lens 43 and tissue surface. As such, a pushing/pulling step of the member 40 may be included as a means to achieve the desired distribution and/or intensity of light energy. In some embodiments, photo-activation includes the step of pushing the member 40 towards the tissue, i.e., closer to the tip 30 of the catheter 1, and then pulling the member 40 back to its original position when the procedure has concluded. When a wider distribution of direct light is needed, then the member may be pulled away from the tissue, i.e., away from the tip 30, and then pushed back to its starting position when the procedure has completed As shown in FIG. 6A and/or FIG. 6B, the light member 40 is positioned beyond an outermost shaft by the light member 40 sliding forwardly towards the tip 30 and over a surface of the outermost shaft. The light member 40 moves parallel to a longitudinal axis; the light member 40 is disposed over the outermost shaft both when the catheter 1 is being delivered to a target location and when the light member 40 is being moved beyond the outermost shaft; the light member 40 is disposed over the outermost shaft both when the catheter 1 is being delivered to a target location and when the light member 40 is being moved further or closer to the tip 30; the light member 40 is configured such that the light member 40 is received over the outermost shaft of the catheter 1 prior to and after the light member 40 is disposed beyond the outermost shaft in the longitudinal direction and while light member 40 is being moved distally to place it beyond the outermost shaft in the longitudinal direction.

According to some embodiments, a light supply for photo-activating substances may be provided by a catheter that is delivered to a treatment site over a guide wire. In these embodiments, a photosensitive material may be previously injected into tissue either directly, e.g., via a needle catheter, or systemically via the bloodstream, followed by placing a light-emitting catheter adjacent to the target tissue. This method for photo-activation may be preferred as it is easier to control the light source, e.g., to control the area of coverage, increase the energy flux per unit area, and/or depth of penetration of light energy to activate photosensitive material.

Figure 7A:
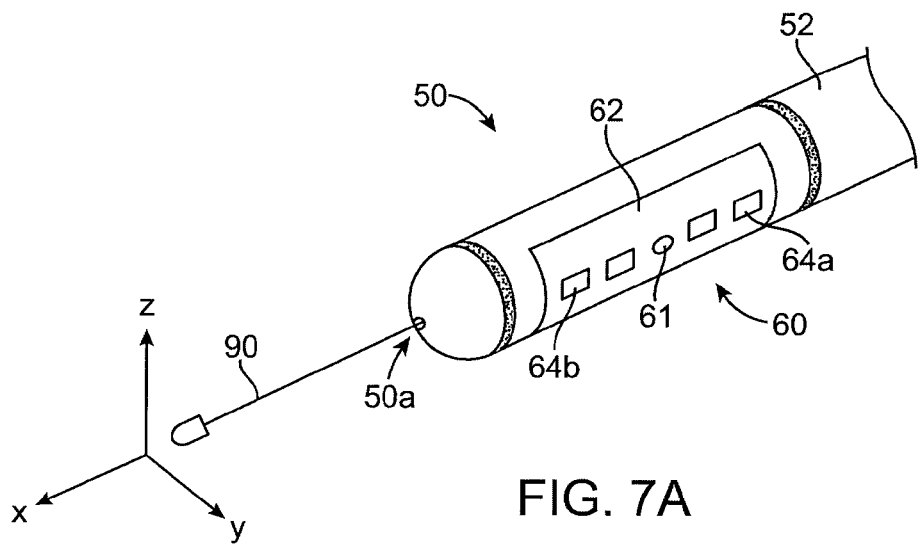
FIGS. 7A and 7B depict a stowed and deployed configuration for a light delivery catheter.
Figure 7B:
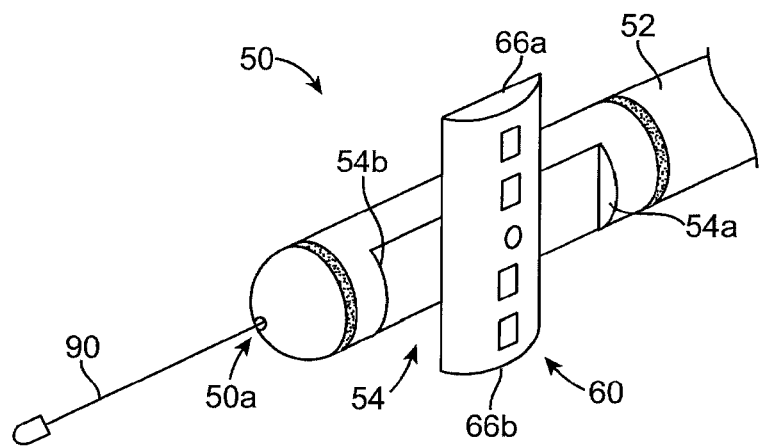

Referring now to FIGS. 7A and 7B there is depicted two perspective views of a light-delivery catheter 50, which may be directed to a treatment site over a guide wire 90. As such, catheter 50 includes a guide wire lumen 50a when delivered via guide wire 90. The catheter 50 may be delivered to a treatment site using standard operating procedures and techniques well known in the art. The catheter 50 may be an over the wire (OTW) or rapid exchange (RX) catheter.

At its distal end 52 catheter 50 includes a pivot arm assembly 60 capable of being moved from a stowed configuration (FIG. 7A) to deployed configuration (FIG. 7B). When deployed a pivot arm 62, which contains an array of light-emitting diodes (LEDs), may be used to illuminate a large area of tissue for purposes of photo-activating a substance deposited or injected in the tissue, or carried thereto by the bloodstream. Pivot assembly 60 includes a pivot axis 61, ends 66a, 66b, and a plurality of LEDs 66 located over the length of the pivot arm 62. Pivot axis 61 may correspond to a post on pivot arm 62 received in a hole formed on the catheter shaft 52, or a hole formed on arm 62 that is received on a post or an annular ring formed on the shaft 52. In some embodiments, the shaft 52 portion of these pivot or hinge connections may cooperate with the arm 62 portion to form a switch that is activated as the arm 62 rotates through a predetermined angle, as discussed below.

The LED elements may be provided by a chip-on-board LED dice, such as those provided by Stocker Yale, Inc., 32

Hampshire Road, Salem, N.H. 03079. This type of LED array can provide tightly packed LEDs that can be fit within the small space provided at a distal end of a catheter that can intravenously be placed in the left ventricle of the heart. The LEDs may be orientated to emit light from one side of a plane, from opposite sides of a plane or from three or four sides, e.g., if a 360 degree light source is desirable. Optics may be utilized to diffuse or collect light emitted from LEDs.

When the catheter 50 is being delivered to a treatment site, pivot arm 62 may be stowed within a recess 54 formed at the distal end of catheter 52. The recess 54 and a leading edge 54b of the recess 54 are such to provide a more streamlined or rounded profile for the catheter 50. This may make the catheter 50 more able to easily maneuver through anatomy when delivered to a treatment site.

FIGS. 8A-8C depict a method of photo-activating target tissue using the catheter 50 of FIG. 7. The guide wire 90 is placed at the appropriate treatment location. The catheter 50 is then delivered to the treatment site by pushing it over the guide wire 90. Once at the treatment location (FIG. 8A), the pivot arm assembly is activated which may include the steps of rotating the pivot arm 62 to the deployed configuration (FIG. 8B), and then energizing the LEDs (FIG. 8C). The later two steps may be performed simultaneously. That is, the LEDs may be automatically energized as the pivot arm 62 is rotated to the position shown in FIG. 8C. The pivot arm 62 may be rotated into a single position, e.g., rotated through 90 degrees, or the pivot arm 62 may be capable of rotating through a desired range of angles. The later embodiments may be desirable as it offers greater control over the tissue for which the direct light is intended. Further, the catheter 50 may include a pair of radiopaque markers 52a, 52b that can aid in determining whether the catheter 50 is orientated properly so that the target tissue will receive a majority of the direct light. The markers may be located on the catheter body 52, the pivot arm 62 or both.

Figure 9A:
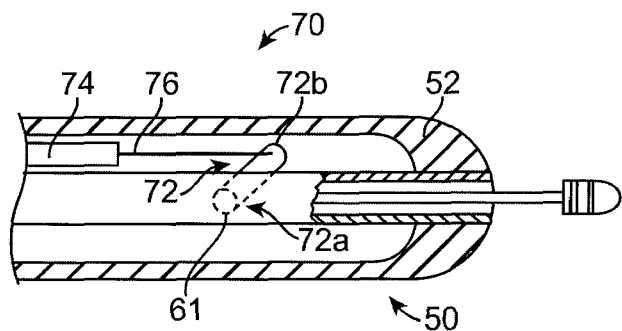
FIG. 9A, 9B illustrate aspects of a first embodiment of a pivot arm assembly for the light delivery catheter of FIG. 7.
Figure 9B:
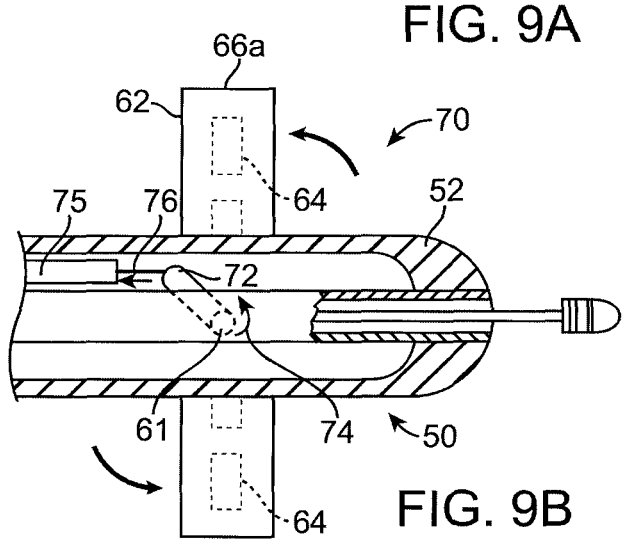

Referring now to FIGS. 9A and 9B, according to some embodiments a mechanism for rotating and activating pivot arm 62 includes a lever 72 coupled to the pivot axis 61 at one end 72a, and to a pull wire 76 at an opposite end 72b. The wire 76 extends through a lumen provided by a tube 75 which extends to a proximal end of the catheter 50. The lever 72 is fixed in rotation relative to the pivot arm 62. A biasing member 74 (e.g., clock, leaf, or linear compression spring) is coupled at one end to the lever 72 and at an opposite end to a catheter inner wall (not shown) or other suitable non-rotating structure. The biasing member biases the pivot arm 62 to a closed or stowed position (i.e., FIG. 7A). The pivot arm 62 may be rotated to the deployed position (FIG. 7B) by pulling on the wire 76 at the catheter proximal end. This will cause the lever to rotate (counterclockwise in FIG. 9B) against the biasing member 74.

The LED chip may be energized by a contact switch. For example, a switch energizing the LED may be activated by forming a switch between end 66a and end 54b. Thus, when the pivot arm is rotated and these two surfaces separate from one another, the LED array is energized. Alternatively, lever 72 may operate as a switch when it is rotated from the position illustrated in FIG. 9A to the position shown in FIG. 9B. In this case, wire 76 is in electrical communication with a metallic lead formed on lever 72, which is in electrical communication with the LED chip. The return path to the power source may be provided by an electrically conducting material formed on a portion of the shaft 52 portion of the arm-shaft pivot. Hence, as the arm 62 rotates through an angle, e.g., 90 degrees, the two electrically conducting surfaces make contact, thereby closing a circuit and energizing the LEDs. For either of these embodiments, the catheter 50 may operate as follows. When the wire 76 is pulled the LED array is energized at the same time that the arm 62 rotates, due to either a surface contact between two surfaces as a result of the arm 62 deployment, or a separation of two surfaces which were in contact when the arm 62 was stowed.

Figure 10A:
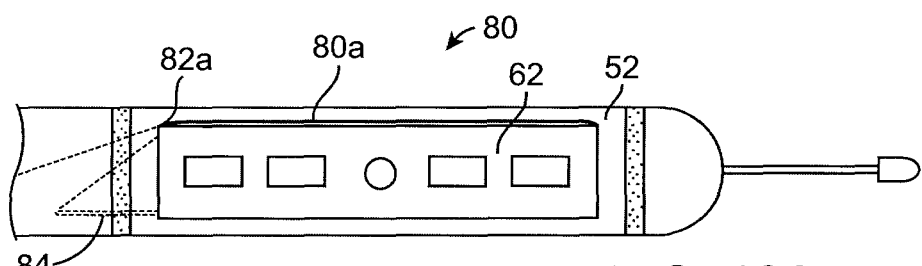
FIG. 10A, 10B illustrate aspects of a second embodiment of a pivot arm assembly for the light delivery catheter of FIG. 7.
Figure 10B:
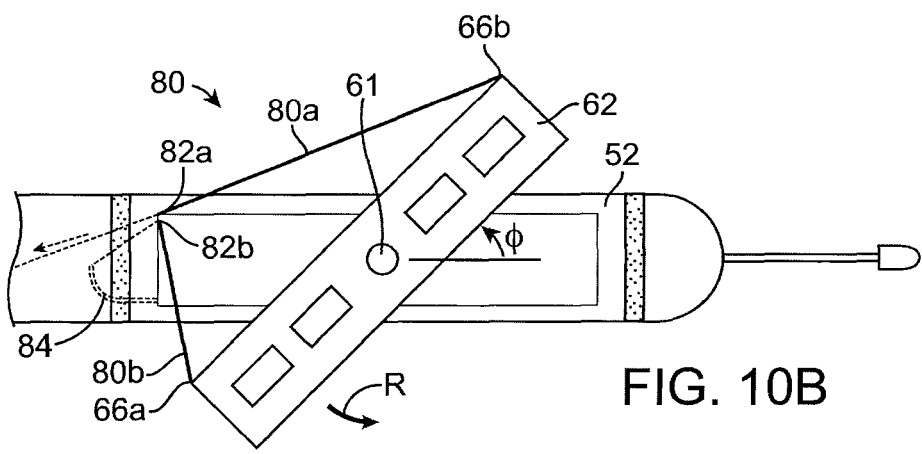

Referring now to FIGS. 10A, 10B, according to other embodiments a mechanism for rotating and activating pivot arm 62 includes a pulley system 80, including a first wire 80a and a second wire 80b. Wires 80a, 80b, may be connected at their distal ends to opposite ends 66a, 66b of the arm 62, i.e., points furthest from the rotation axis 61. The wires 80a, 80b extend from ends 66 to the interior of the catheter shaft 52. Wire 80a extends through an aperture 82a, and wire 80b extends through the same, or nearby aperture 82b. Wire 80b is intended to provide a biasing force when the arm 62 is deployed. As depicted, wire 80b is secured to a flex member 84 which extends straight when arm 62 is stowed and bends upward when arm 62 is deployed. Accordingly, the strain energy in the flexed member 74 provides a biasing force that places the arm 62 back in its stowed position when the wire tension is relieved. Wire 80a extends to a proximal end or is coupled to other structure that enables a pull force to be applied to the wire 80a by an operator, at the proximal end of the catheter 50. Wire 80a and 80b may be used to connect the LED chip to a power source to activate the LEDs. The arm 62 may be rotated through an operator-selected angle θ. This angle control may be desirable for cases in which the catheter body 52 orientation within the body cavity, e.g., left ventricle, is such that the angular orientation of the arm 62 relative to the body 52 needs adjustment.

As will be appreciated, the invention may be practiced using a variety of catheters. Examples of catheters that may incorporate one or more aspects of the invention include those disclosed in U.S. Publication No. 2005/0070844, U.S. Publication No. 2007/0167822 and U.S. application Ser. No. 12/022,047 filed Jan. 29, 2008.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A catheter having distal and proximal ends, comprising:
   an outermost shaft secured to a catheter tip, the tip having an opening;
   a light member configured as a tube, received over the outermost shaft and disposed adjacent the distal end, wherein the light member is movable relative to the outermost shaft;
   a piercing needle at the distal end, disposed within the outermost shaft and coupled to an actuator for displacing the needle through the opening;
   wherein the light member includes a plurality of fiber optic strands having respective light-emitting ends disposed at the distal end of the tube, the light-emitting ends being arranged to circumscribe a longitudinal axis of the piercing needle;
   wherein the light member is configured for being displaced beyond the outermost shaft in the longitudinal direction; and
   wherein the actuator is configured for displacing the needle through the opening while the light member is disposed beyond the outermost shaft in the longitudinal direction.

2. The catheter of claim 1,
wherein the needle includes a body having a piercing tip disposed at the distal end and a proximal end configured for being selectively placed in fluid communication with a substance, wherein the body forms a lumen for delivery of the substance from the proximal end to an exit located adjacent to the tip; and
the light member has a proximal end optically coupled to an extracorporeal light source.

3. The catheter of claim 1, wherein the light member is configurable between a deployed and/or stowed position.

4. The catheter of claim 1, wherein the light member is configured to emit light such that a region that surrounds the needle receives direct light from the light member.

5. The catheter of claim 1, wherein the catheter has a longitudinal axis at its distal end, and the light emitting ends are orientated to emit light substantially along the longitudinal axis.

6. The catheter of claim 1, wherein the light emitting ends have a concave lens type.

7. The catheter of claim 1, wherein the light member is positioned beyond the outermost shaft by the tube sliding forwardly towards the tip and over a surface of the outermost shaft wherein the light member moves parallel to the longitudinal axis.

8. The catheter of claim 1, wherein the light member is disposed over the outermost shaft both when the catheter is being delivered to a target location and when the light member is being moved beyond the outermost shaft.

9. The catheter of claim 1, wherein the light member is configured such that the light member is received over the outermost shaft of the catheter prior to and after the light member is disposed beyond the outermost shaft in the longitudinal direction, and while the light member is being moved distally to place it beyond the outermost shaft in the longitudinal direction.

10. A catheter having distal and proximal ends, comprising:
an outermost shaft secured to a catheter tip, the tip having an opening;
a tubular light member received over the outermost shaft and disposed adjacent the distal end, wherein the light member is movable relative to the outermost shaft;
a piercing needle at the distal end, disposed within the outermost shaft and coupled to an actuator for displacing the needle through the opening;
wherein the light member includes a plurality of fiber optic strands having respective light-emitting ends disposed at the distal end of the catheter and arranged so as to circumscribe a longitudinal axis of the piercing needle;
wherein the light member may be selectively moved closer or further from a tip of the needle by operation of a controller disposed at the proximal end, the controller including a guide for correlating a displacement of the light member relative to the catheter tip to the surface area of tissue receiving direct light when the catheter tip is abutting the tissue surface.

11. The catheter of claim 10, wherein the light member is configured for being displaced beyond the outermost shaft; and wherein the actuator is configured for displacing the needle through the opening while the light member is disposed beyond the outermost shaft.

12. The catheter of claim 10, wherein the light member is disposed over the outermost shaft both when the catheter is being delivered to a target location and when the light member is being moved further or closer to the tip.

* * * * *